US010730876B2

(12) United States Patent
Ibrahim et al.

(10) Patent No.: US 10,730,876 B2
(45) Date of Patent: *Aug. 4, 2020

(54) SYNTHESIS OF A COMPOUND THAT MODULATES KINASES

(71) Applicants: Plexxikon Inc., Berkeley, CA (US); Daiichi Sankyo Company, Limited, Tokyo (JP)

(72) Inventors: Prabha N. Ibrahim, Mountain View, CA (US); Masayoshi Jin, Tokyo (JP); Shinji Matsuura, Tokyo (JP)

(73) Assignees: Plexxikon Inc., Berkeley, CA (US); Daiichi Sankyo Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/510,617

(22) Filed: Jul. 12, 2019

(65) Prior Publication Data

US 2019/0337943 A1 Nov. 7, 2019

Related U.S. Application Data

(60) Continuation of application No. 16/024,197, filed on Jun. 29, 2018, now Pat. No. 10,399,975, which is a division of application No. 15/665,804, filed on Aug. 1, 2017, now Pat. No. 10,040,792, which is a division of application No. 15/147,709, filed on May 5, 2016, now Pat. No. 9,745,298.

(60) Provisional application No. 62/241,040, filed on Oct. 13, 2015, provisional application No. 62/157,902, filed on May 6, 2015.

(51) Int. Cl.
*C07D 471/04* (2006.01)

(52) U.S. Cl.
CPC .................. *C07D 471/04* (2013.01)

(58) Field of Classification Search
None
See application file for complete search history.

(56) References Cited

U.S. PATENT DOCUMENTS

| | | | |
|---|---|---|---|
| 7,202,266 B2 | 4/2007 | Arnold et al. |
| 7,348,338 B2 | 3/2008 | Arnold et al. |
| 7,476,746 B2 | 1/2009 | Artis et al. |
| 7,491,831 B2 | 2/2009 | Artis et al. |
| 7,504,509 B2 | 3/2009 | Ibrahim et al. |
| 7,517,970 B2 | 4/2009 | West |
| 7,572,806 B2 | 8/2009 | Arnold et al. |
| 7,585,859 B2 | 9/2009 | Ibrahim et al. |
| 7,605,168 B2 | 10/2009 | Ibrahim et al. |
| 7,723,374 B2 | 5/2010 | Artis et al. |
| 7,759,475 B2 | 7/2010 | West |
| 7,846,941 B2 | 12/2010 | Zhang et al. |
| 7,863,288 B2 | 1/2011 | Ibrahim et al. |
| 7,893,075 B2 | 2/2011 | Zhang et al. |
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Ibrahim et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,470,821 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |
| 8,865,735 B2 | 10/2014 | Ibrahim et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 9,096,593 B2 | 8/2015 | Zhang et al. |
| 9,150,570 B2 | 10/2015 | Ibrahim |
| 9,169,250 B2 | 10/2015 | Zhang et al. |
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |

(Continued)

FOREIGN PATENT DOCUMENTS

WO WO-2008/063888 5/2008
WO WO-2008064255 5/2008

(Continued)

OTHER PUBLICATIONS

U.S. Appl. No. 16/123,612, filed Sep. 6, 2018, Desai et al.

(Continued)

*Primary Examiner* — Zinna Northington Davis
(74) *Attorney, Agent, or Firm* — Sheppard Mullin Richter & Hampton LLP

(57) ABSTRACT

The present disclosure provides processes for the preparation of a compound of formula I:

or a salt thereof, active on the receptor protein kinases c-Kit and/or c-Fms and/or Flt3. The disclosure also provides compounds and processes for the preparation of the compounds that are synthetic intermediates to the compound of formula I.

5 Claims, No Drawings

(56) References Cited

U.S. PATENT DOCUMENTS

| | | | |
|---|---|---|---|
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 9,663,517 B2 | 5/2017 | Desai et al. |
| 9,676,748 B2 | 6/2017 | Wu et al. |
| 9,682,981 B2 | 6/2017 | Zhang et al. |
| 9,695,169 B2 | 7/2017 | Ibrahim |
| 9,718,847 B2 | 8/2017 | Zhang et al. |
| 9,730,918 B2 | 8/2017 | Bollag et al. |
| 9,745,298 B2 | 8/2017 | Ibrahim et al. |
| 9,771,363 B2 | 9/2017 | Ibrahim et al. |
| 9,771,369 B2 | 9/2017 | Lin et al. |
| 9,822,109 B2 | 11/2017 | Zhang et al. |
| 9,975,894 B2 | 5/2018 | Ibrahim et al. |
| 9,994,567 B2 | 6/2018 | Ibrahim et al. |
| 10,040,792 B2 | 8/2018 | Ibrahim et al. |
| 10,399,975 B2 * | 9/2019 | Ibrahim ............... C07D 471/04 |
| 10,435,404 B2 | 10/2019 | Ibrahim et al. |
| 2014/0128390 A1 | 5/2014 | Lin et al. |
| 2014/0357612 A1 | 12/2014 | Zhang et al. |
| 2016/0075712 A1 | 3/2016 | Shi et al. |
| 2016/0326162 A1 | 11/2016 | Lin et al. |
| 2016/0326168 A1 | 11/2016 | Ibrahim et al. |
| 2016/0339025 A1 | 11/2016 | Ibrahim et al. |
| 2016/0340357 A1 | 11/2016 | Ibrahim et al. |
| 2016/0340358 A1 | 11/2016 | Ibrahim |
| 2017/0029413 A1 | 2/2017 | Holladay et al. |
| 2017/0056382 A1 | 3/2017 | Wu et al. |
| 2017/0081326 A1 | 3/2017 | Ibrahim et al. |
| 2017/0157120 A1 | 6/2017 | Ibrahim et al. |
| 2017/0158690 A1 | 6/2017 | Wu et al. |
| 2017/0247370 A1 | 8/2017 | Zhang et al. |
| 2017/0267660 A1 | 9/2017 | Lin et al. |
| 2017/0283423 A1 | 10/2017 | Zhang et al. |
| 2017/0319559 A1 | 11/2017 | Wu et al. |
| 2017/0320899 A1 | 11/2017 | Zhang et al. |
| 2017/0334909 A1 | 11/2017 | Ibrahim et al. |
| 2017/0349572 A1 | 12/2017 | Wu et al. |
| 2018/0030051 A1 | 2/2018 | Ibrahim et al. |
| 2018/0055828 A1 | 3/2018 | Bollag et al. |
| 2018/0072722 A1 | 3/2018 | Zhang et al. |
| 2018/0099939 A1 | 4/2018 | Zhang et al. |
| 2018/0099975 A1 | 4/2018 | Zhang et al. |
| 2018/0111929 A1 | 4/2018 | Ibrahim et al. |
| 2018/0111930 A1 | 4/2018 | Desai et al. |
| 2018/0215763 A1 | 8/2018 | Wu et al. |
| 2018/0265508 A1 | 9/2018 | Lin et al. |
| 2018/0327403 A1 | 11/2018 | Ibrahim et al. |
| 2018/0354946 A1 | 12/2018 | Zhang et al. |
| 2019/0119273 A1 | 4/2019 | Ibrahim et al. |
| 2019/0125747 A1 | 5/2019 | Rezaei et al. |
| 2019/0161484 A1 | 5/2019 | Ibrahim et al. |
| 2019/0175567 A1 | 6/2019 | Wu et al. |
| 2019/0209536 A1 | 7/2019 | Wu et al. |
| 2019/0300487 A1 | 10/2019 | Zhang et al. |
| 2019/0337943 A1 | 11/2019 | Ibrahim et al. |
| 2019/0337944 A1 | 11/2019 | Ibrahim et al. |
| 2019/0367507 A1 | 12/2019 | Ibrahim et al. |
| 2020/0010465 A1 | 1/2020 | Ibrahim et al. |

FOREIGN PATENT DOCUMENTS

| | | |
|---|---|---|
| WO | WO-2011/057022 | 5/2011 |
| WO | WO-2012158957 | 11/2012 |
| WO | WO-2013/142427 | 9/2013 |

OTHER PUBLICATIONS

U.S. Appl. No. 16/148,244, filed Oct. 1, 2018, Zhang et al.
U.S. Appl. No. 16/358,608, filed Mar. 19, 2019, Zhang et al.
U.S. Appl. No. 16/400,801, filed May 1, 2019, Ibrahim et al.
U.S. Appl. No. 16/441,610, filed Jun. 14, 2019, Ibrahim et al.
International Preliminary Report on Patentability for International Application No. PCT/US2016/031022 dated Nov. 7, 2017. (8 pages).
International Search Report and Written Opinion for International Application No. PCT/US2016/031022 dated Jul. 13, 2016. (13 pages).
U.S. Appl. No. 16/563,656, filed Sep. 6, 2019, Zhang et al.
U.S. Appl. No. 16/684,198, filed Nov. 14, 2019, Desai et al.
U.S. Appl. No. 16/687,015, filed Nov. 18, 2019, Zhang et al.
U.S. Appl. No. 16/706,497, filed Dec. 6, 2019, Ibrahim et al.
U.S. Appl. No. 16/749,893, filed Jan. 22, 2020, Ibrahim et al.
U.S. Appl. No. 16/814,632, filed Mar. 10, 2020, Wu et al.
Extended European search report for European Application 19189460.9 dated Oct. 2, 2019. (7 pages).

* cited by examiner

SYNTHESIS OF A COMPOUND THAT MODULATES KINASES

CROSS-REFERENCE TO RELATED APPLICATIONS

This application is a continuation of U.S. application Ser. No. 16/024,197, filed Jun. 29, 2018, now U.S. Pat. No. 10,399,975, which is a divisional of U.S. application Ser. No. 15/665,804, filed Aug. 1, 2017, now U.S. Pat. No. 10,040,792, which is a divisional of U.S. application Ser. No. 15/147,709, filed May 5, 2016, now U.S. Pat. No. 9,745,298, which application claims the benefit under 35 U.S.C. § 119(e) to U.S. Provisional Application No. 62/157,902, filed May 6, 2015, and U.S. Provisional Application No. 62/241,040, filed Oct. 13, 2015, all of which are incorporated herein by reference in their entireties.

FIELD

The present disclosure relates generally to the field of organic synthetic methodology for the preparation of compounds modulating kinases and their synthetic intermediates.

BACKGROUND

The compound named, [5-(5-chloro-1H-pyrrolo[2,3-b]pyridin-3-ylmethyl)-pyridin-2-yl]-(6-trifluoromethyl-pyridin-3-ylmethyl)-amine, which is also known as pexidartinib, is effective for treating subjects suffering from or at risk of a c-Kit and/or c-Fms and/or Flt3 mediated disease or condition. Suitable compounds, including pexidartinib or a salt thereof, for the treatment of such diseases and conditions are disclosed in U.S. Pat. No. 7,893,075, U.S. Publication No. 2014-0037617 and U.S. Publication No. 2013-0274259, the disclosures of all of which are incorporated herein by reference in their entirety.

There remains a need in developing new versatile and facile processes for the efficient preparation of pexidartinib and other similar molecules, especially in an industrial scale.

SUMMARY

The present disclosure provides in one embodiment a process for making a compound of formula I, named [5-(5-chloro-1H-pyrrolo[2,3-b]pyridin-3-ylmethyl)-pyridin-2-yl]-(6-trifluoromethyl-pyridin-3-ylmethyl)-amine:

I

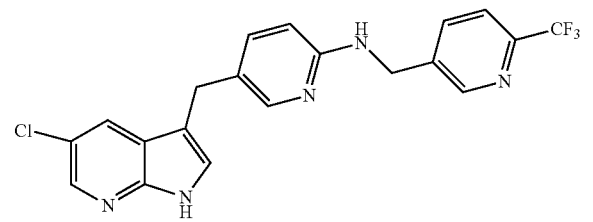

or a salt thereof.

In another embodiment, this disclosure provides a process for making a compound of formula II, named [5-(5-chloro-1H-pyrrolo[2,3-b]pyridin-3-ylmethyl)-pyridin-2-yl]-(6-trifluoromethyl-pyridin-3-ylmethyl)-amine HCl salt:

II

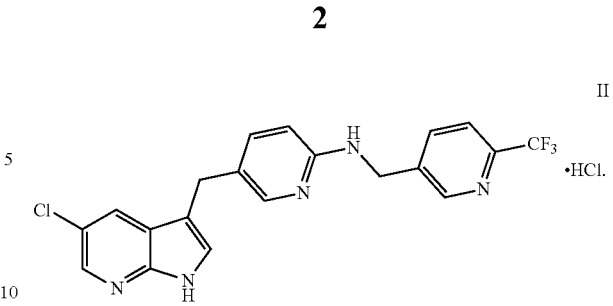

In another embodiment, this disclosure provides a process for preparation of a compound of formula III:

III

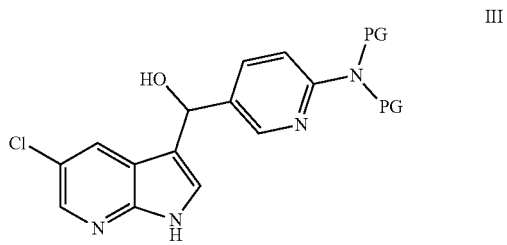

or a salt thereof;

comprising contacting a compound of formula A or a salt thereof, with a compound of formula B or a salt thereof:

A

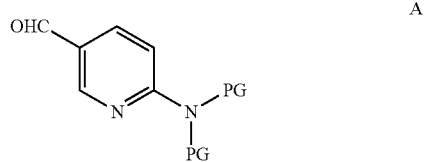

B

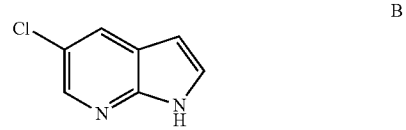

under addition conditions to provide the compound of formula III or a salt thereof, wherein each PG independently is a protecting group.

In another embodiment, this disclosure provides a process for preparation of a compound of formula IV:

IV

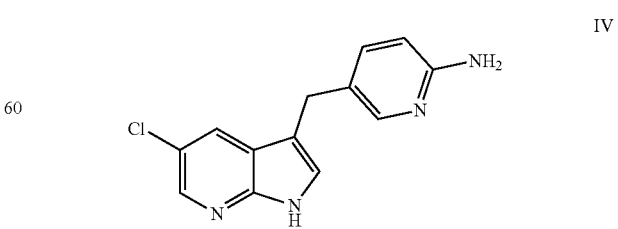

or a salt thereof;

comprising subjecting a compound of formula III:

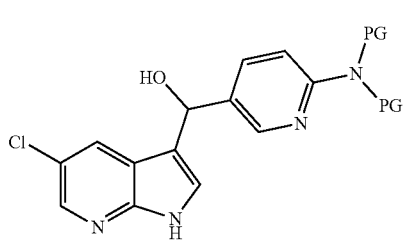

or a salt thereof, to N-deprotection and alcohol reduction conditions to provide the compound of formula IV or a salt thereof, wherein each PG independently is a protecting group. In another embodiment, this disclosure provides a process for preparation of a compound of formula I:

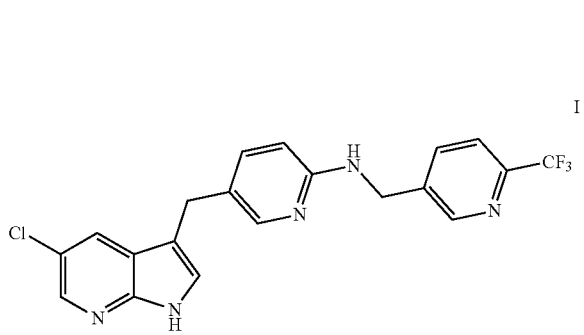 [SMILES: FC(F)(F)c1ccc(CNc2ccc(Cc3c[nH]c4ncc(Cl)cc34)cn2)cn1]

or a salt thereof;
comprising contacting a compound of formula IV:

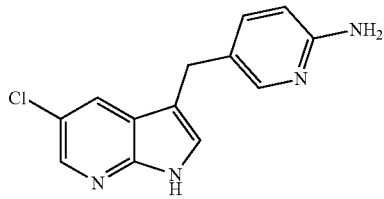

or a salt thereof;
with a compound of formula V:

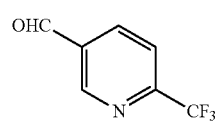

or a salt thereof,
under reductive amination conditions to provide the compound of formula I or a salt thereof.

In another embodiment, this disclosure provides a process for preparation of a compound of formula I:

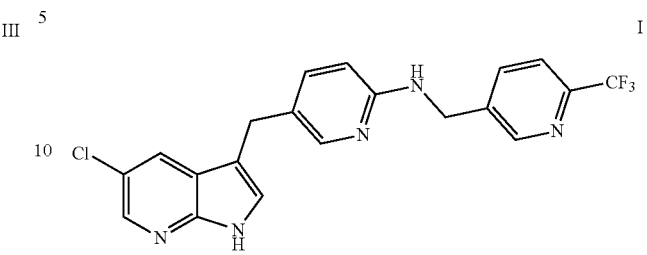

or a salt thereof, comprising:
a) contacting a compound of formula A or a salt thereof, with a compound of formula B or a salt thereof:

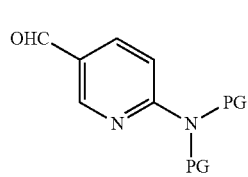

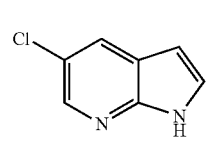

under addition conditions to provide a compound of formula III:

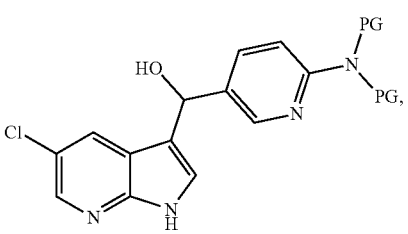

or a salt thereof;
b) subjecting the compound of formula III or a salt thereof, to N-deprotection and alcohol reduction conditions to provide a compound of formula IV:

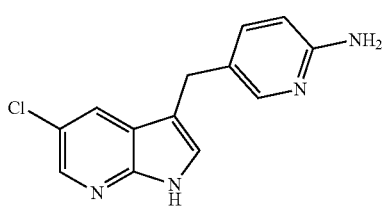

or a salt thereof; and c) contacting the compound of formula IV or a salt thereof with a compound of formula V:

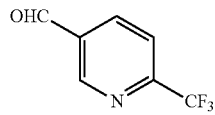

or a salt thereof,
under reductive amination conditions to provide the compound of formula I or a salt thereof, wherein each PG independently is a protecting group.

In another embodiment, this disclosure provides a process for preparation of a compound of formula II, named [5-(5-chloro-1H-pyrrolo[2,3-b]pyridin-3-ylmethyl)-pyridin-2-yl]-(6-trifluoromethyl-pyridin-3-ylmethyl)-amine HCl salt:

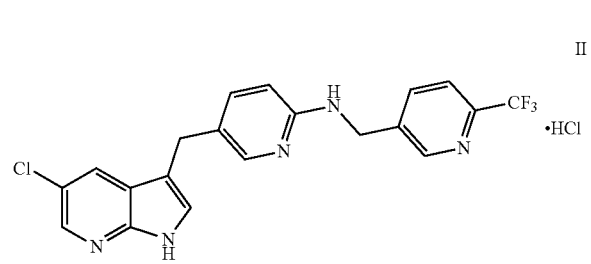 [SMILES: FC(F)(F)c1ccc(CNc2ccc(Cc3c[nH]c4ncc(Cl)cc34)cn2)cn1 ; Cl]

comprising:
a) contacting a compound of formula A or a salt thereof, with a compound of formula B or a salt thereof:

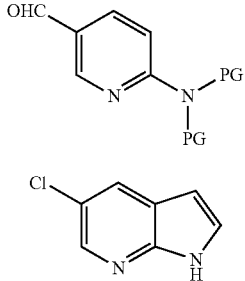

under addition conditions to provide a compound of formula III:

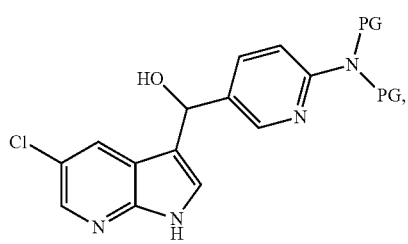

or a salt thereof;
b) subjecting the compound of formula III or a salt thereof, to N-deprotection and alcohol reduction conditions to provide a compound of formula IV:

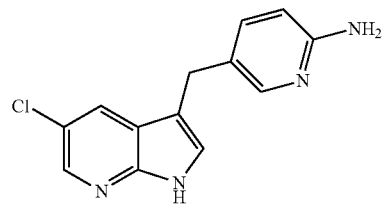

or a salt thereof;
c) contacting the compound of formula IV or a salt thereof with a compound of formula V:

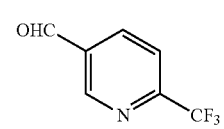

or a salt thereof,
under reductive amination conditions to provide the compound of formula I:

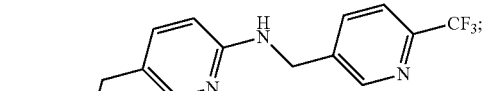

and
d) reacting the compound of formula I with HCl to provide the compound of formula II, wherein each PG independently is a protecting group.

In another embodiment, this disclosure provides a compound of formula III:

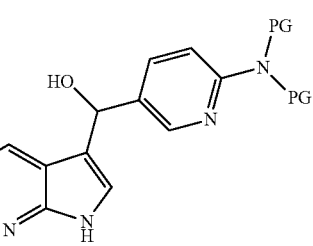

or a salt thereof, wherein each PG independently is a protecting group.

In another embodiment, this disclosure provides a compound of formula IIIa:

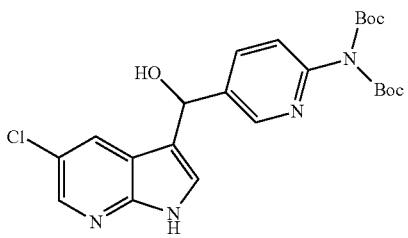

IIIa or a salt thereof.

In another embodiment, this disclosure provides a compound of formula IV:

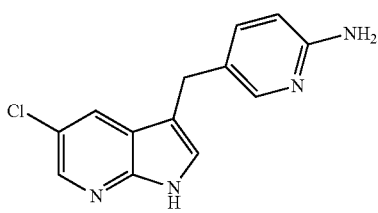

IV or a salt thereof.

More specific embodiments are described below.

DETAILED DESCRIPTION

Definitions

As used herein the following definitions apply unless clearly indicated otherwise.

All atoms designated within a formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^1C$, $^{12}C$, $^{13}C$, $^{14}C$; oxygen includes for example $^{16}O$, $^{17}O$, $18O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

Certain compounds contemplated for use in accordance with the present disclosure can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate, hemi-hydrate, channel hydrate etc. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure.

Certain compounds contemplated for use in accordance with the present disclosure may exist in multiple crystalline or amorphous forms. In general, all physical forms are equivalent for the uses contemplated by the present disclosure and are intended to be within the scope of the present disclosure.

As used herein, the term "salt" refers to acid addition salts and basic addition salts. Examples acid addition salts include those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid. Basic addition salts include those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, 19$^{th}$ ed., Mack Publishing Co., Easton, Pa., Vol. 2, p. 1457, 1995. Such salts can be prepared using the appropriate corresponding bases.

The term "USP water" means water is the subject of an official monograph in the current US Pharmacopeia.

Compounds can be formulated as or be in the form of a salt, including pharmaceutically acceptable salts. Contemplated salt forms include, without limitation, mono, bis, tris, tetrakis, and so on. The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

Thus, for example, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

The pharmaceutically acceptable salt of the different compounds may be present as a complex. Examples of complexes include 8-chlorotheophylline complex (analogous to, e.g., dimenhydrinate:diphenhydramine 8-chlorotheophylline (1:1) complex; Dramamine) and various cyclodextrin inclusion complexes.

Unless specified to the contrary, specification of a compound herein includes pharmaceutically acceptable salts of such compound.

As used herein, the term "addition conditions" refers to the reaction conditions under which an aryl halide adds to an aryl aldehyde. The "addition conditions" as disclosed herein typically comprise a base and a catalyst. The non-limiting examples of the base include sodium carbonate, sodium bicarbonate, potassium carbonate, potassium bicarbonate, potassium-tert-butoxide, potassium tert-pentoxide, cesium carbonate, lithium-tert-butoxide, magnesium-tert-butoxide, sodium-tert-butoxide, potassium hydroxide, lithium hydroxide and the like. The addition conditions typically comprise a temperature ranging from about 0° C. to about −10° C. and reaction time of about 24 hours. The non-limiting examples of the catalyst include tetrabutylammonium hydrogen sulfate, tetrabutylammonium fluoride, tetrabutylammonium chloride, tetrabutylammonium bromide, tetrabutylammonium iodide, 18-crown-6 and 15-crown-5.

As used herein, the term "reductive amination conditions" refers to the reaction conditions under which a carbonyl group is converted to an amine via reduction of the intermediate imine. The imine formation and reduction occur sequentially in one pot. "Reductive amination conditions" as disclosed herein typically comprise triethylsilane and trifluoroacetic acid. The reductive amination conditions typically further comprise addition of trifluoroacetic acid at a temperature ranging from about 0° C. to about −10° C. followed by stirring for about 6 hours followed by addition of triethylsilane and refluxing for about 24 hours. The non-limiting examples of reductive amination conditions include sodium borohydride and benzoic acid; sodium triacetoxyborohydride and acetic acid; and the like.

As used herein, the term "protecting group" refers to a moiety of a compound that masks or alters the properties of a functional group or the properties of the compound as a whole. The chemical substructure of a protecting group varies widely. One function of a protective group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive. The non-limiting examples of protecting groups for an amine include t-butyloxycarbonyl (Boc), benzyloxycarbonyl (Cbz), 9-fluorenylmethoxycarbonyl (Fmoc), and the like.

As used herein, the term "N-deprotection and alcohol reduction conditions" refers to the reaction conditions under which a protecting group from an amine is removed and a CH(OH) group is reduced to a $CH_2$ group. These two transformations can be done in one step or two separate steps, namely, "N-deprotection conditions" and "alcohol reduction conditions." "N-deprotection and alcohol reduction conditions" as disclosed herein, when done in one step, typically comprise triethylsilane and trifluoroacetic acid. The N-deprotection and alcohol reduction conditions typically further comprise addition of a triorganosilane such as triethylsilane and trifluoroacetic acid at an initial temperature of about 0-10° C. followed stirring for about 24 hours at room temperature followed by refluxing for about 8 hours.

As used herein, the term "N-deprotection conditions" refers to the reaction conditions under which a protecting group from an amine is removed. The non-limiting examples of protective groups for an amine include tert-butyloxycarbonyl (Boc), benzyloxycarbonyl (Cbz), 9-fluorenylmethoxycarbonyl (Fmoc), and the like. The N-deprotection conditions for Boc include using an acid such as HCl, methanesulfonic acid, para-toluenesulfonic acid, and the like. The N-deprotection conditions for Cbz include hydrogenation using hydrogen and a catalyst such as Pd and the like. The N-deprotection conditions for Fmoc include using a base such as 1,8-diazabicyclo[5.4.0]undec-7-ene (DBU), piperidine, and the like.

As used herein, the term "alcohol reduction conditions" refers to the reaction conditions under which a CH(OH) group is reduced to a $CH_2$ group. The "alcohol reduction conditions" include chlorodipohenylsilane with $InCl_3$; triethylsilane and a catalyst; and the like.

In addition, abbreviations as used herein have respective meanings as follows:

| | |
|---|---|
| br | broad |
| D | doublet |
| DMSO | dimethylsulfoxide |
| Eq | equivalent |
| gm | gram |
| HPLC | high pressure liquid chromatography |
| kg | kilogram |
| L | liter |
| mL | milliliter |
| MTBE | methyl t-butyl ether |
| NMR | nuclear magnetic resonance |
| S | singlet |
| TFA | trifluoroacetic acid |
| vol | volume |

Process

As described generally above, the disclosure provides in some embodiments a process for making a compound of formula I. In another embodiment, the disclosure provides processes for making intermediates for the compound of formula I.

The present disclosure provides in one embodiment a process for making a compound of formula I, named [5-(5-chloro-1H-pyrrolo[2,3-b]pyridin-3-ylmethyl)-pyridin-2-yl]-(6-trifluoromethyl-pyridin-3-ylmethyl)-amine:

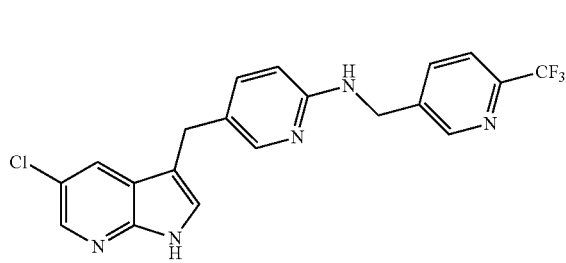

or a salt thereof.

In another embodiment, this disclosure provides a process for preparation of a compound of formula I, named [5-(5-chloro-1H-pyrrolo[2,3-b]pyridin-3-ylmethyl)-pyridin-2-yl]-(6-trifluoromethyl-pyridin-3-ylmethyl)-amine:

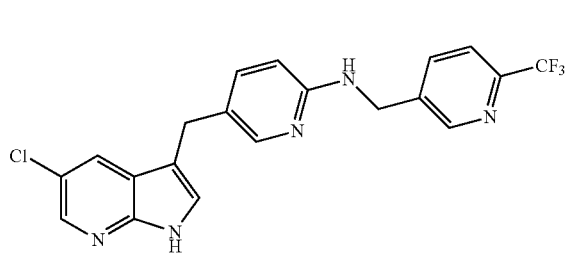

or a salt thereof, comprising:
a) contacting a compound of formula A or a salt thereof, with a compound of formula B or a salt thereof:

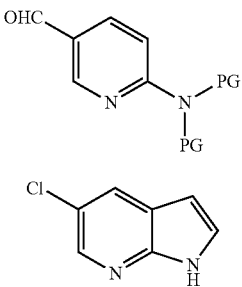

under addition conditions to provide a compound of formula III:

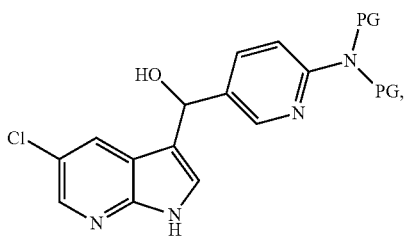

or a salt thereof;
b) subjecting the compound of formula III or a salt thereof, to N-deprotection and alcohol reduction conditions to provide a compound of formula IV:

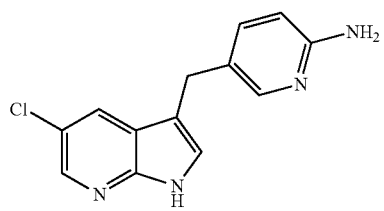

or a salt thereof; and
c) contacting the compound of formula IV or a salt thereof with a compound of formula V:

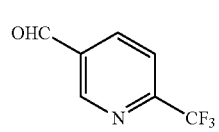

or a salt thereof,
under reductive amination conditions to provide the compound of formula I or a salt thereof, wherein each PG independently is a protecting group.

The addition conditions of step a) comprise a base and a catalyst. The non-limiting examples of the base include sodium carbonate, sodium bicarbonate, potassium carbonate, potassium bicarbonate, potassium-tert-butoxide, potassium tert-pentoxide, cesium carbonate, lithium-tert-butoxide, magnesium-tert-butoxide, sodium-tert-butoxide, potassium hydroxide and lithium hydroxide. The non-limiting examples of the catalyst include tetrabutylammonium hydrogen sulfate, tetrabutylammonium fluoride, tetrabutylammonium chloride, tetrabutylammonium bromide, tetrabutylammonium iodide, 18-crown-6 and 15-crown-5.

The addition conditions of step a) further comprise a solvent. The non-limiting examples of the solvent include isopropyl alcohol, toluene, acetonitrile, nitromethane, N,N-dimethylformamide, N,N-dimethylacetamide, dimethylsulfoxide, 3-methyl-1-butanol, 2-methoxyethanol, 2-propanol, and xylene.

The addition conditions of step a) further comprise a temperature of about 15-25° C.

A variety of protecting groups, PG, can be used in compound of formula A. The non-limiting examples of protecting groups for amines include t-butyloxycarbonyl (Boc), benzyloxycarbonyl (Cbz), 9-fluorenylmethoxycarbonyl (Fmoc), and the like. In one embodiment, PG is Boc. The N-deprotection conditions of step b) refer to conditions under which the protective group, P, is removed. In one embodiment, PG is Boc and the N-deprotecting conditions comprise an acid such as HCl, methanesulfonic acid, toluenesulfonic acids, and the like. In one embodiment, the acid is para-toluenesulfonic acid.

The N-deprotection and alcohol reduction conditions of step b) comprise triethylsilane and trifluoroacetic acid.

The N-deprotection and alcohol reduction conditions of step b) further comprise a solvent. The non-limiting examples of the solvent include acetonitrile, 1,2-dichloroethane, dichloromethane, tetrahydrofuran, 1,2-dimethoxyethane, butyl acetate, acetone, 2-butanone, and dimethylsulfoxide.

The reductive amination conditions of step c) comprise triethylsilane and trifluoroacetic acid.

The reductive amination conditions of step c) further comprise a solvent. The non-limiting examples of the solvent include acetonitrile, 1,2-dichloroethane, dichloromethane, tetrahydrofuran, 1,2-dimethoxyethane, butyl acetate, acetone, acetonitrile, 2-butanone, and dimethylsulfoxide.

In another embodiment, this disclosure provides a process for preparation of a compound of formula compound of formula II:

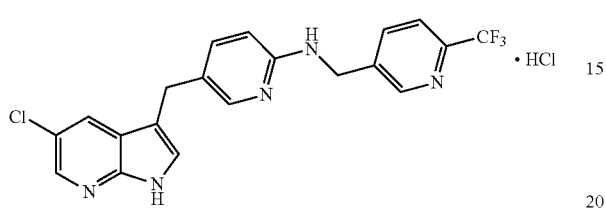

II

· HCl comprising:
a) contacting a compound of formula A or a salt thereof, with a compound of formula B or a salt thereof:

A

B under addition conditions to provide a compound of formula III:

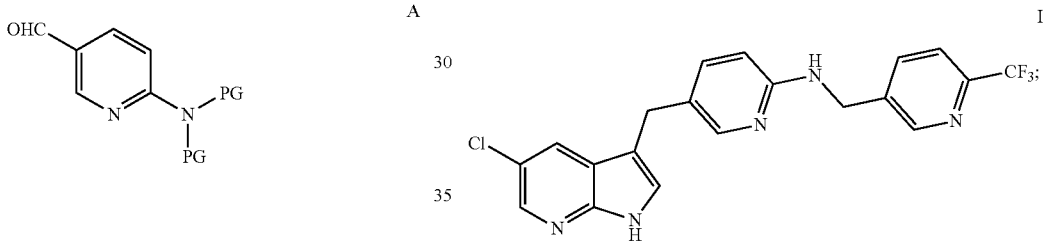

III or a salt thereof;
b) subjecting the compound of formula III or a salt thereof, to N-deprotection and alcohol reduction conditions to provide a compound of formula IV:

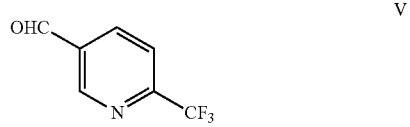 [SMILES: O=Cc1ccc(C(F)(F)F)nc1]

IV or a salt thereof;
c) contacting the compound of formula IV or a salt thereof with a compound of formula V:

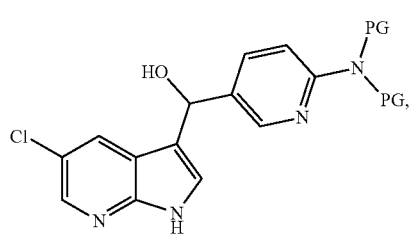

V or a salt thereof,
under reductive amination conditions to provide the compound of formula I:

I and
d) reacting the compound of formula I with HCl to provide the compound of formula II wherein each PG independently is a protecting group.

The addition conditions of step a) comprise a base and a catalyst. The non-limiting examples of the base include sodium carbonate, sodium bicarbonate, potassium carbonate, potassium bicarbonate, potassium-tert-butoxide, potassium tert-pentoxide, cesium carbonate, lithium-tert-butoxide, magnesium-tert-butoxide, sodium-tert-butoxide, potassium hydroxide and lithium hydroxide. The non-limiting examples of the catalyst include tetrabutylammonium hydrogen sulfate, tetrabutylammonium fluoride, tetrabutylammonium chloride, tetrabutylammonium bromide, tetrabutylammonium iodide, 18-crown-6 and 15-crown-5.

The addition conditions of step a) further comprise a solvent. The non-limiting examples of the solvent include isopropyl alcohol, toluene, acetonitrile, nitromethane, N,N-dimethylformamide, N,N-dimethylacetamide, dimethylsulfoxide, 3-methyl-1-butanol, 2-methoxyethanol, 2-propanol, and xylene.

The addition conditions of step a) further comprise a temperature of about 15-25° C.

A variety of protecting groups, PG, can be used in compound of formula A. The non-limiting examples of protecting groups for amines include t-butyloxycarbonyl (Boc), benzyloxycarbonyl (Cbz), 9-fluorenylmethoxycarbonyl (Fmoc), and the like. In one embodiment, PG is Boc. The N-deprotection conditions of step b) refer to conditions under which the protective group, P, is removed. In one embodiment, PG is Boc and the N-deprotecting conditions comprise an acid such as HCl, methanesulfonic acid, toluenesulfonic acids, and the like. In one embodiment, the acid is para-toluenesulfonic acid.

The N-deprotection and alcohol reduction conditions of step b) comprise triethylsilane and trifluoroacetic acid.

The N-deprotection and alcohol reduction conditions of step b) further comprise a solvent. Non-limiting examples of the solvent include acetonitrile, 1,2-dichloroethane, dichloromethane, tetrahydrofuran, 1,2-dimethoxyethane, butyl acetate, acetone, 2-butanone, and dimethylsulfoxide.

The reductive amination conditions of step c) comprise triethylsilane and trifluoroacetic acid.

The reductive amination conditions of step c) further comprise a solvent. The non-limiting examples of the solvent include acetonitrile, 1,2-dichloroethane, dichloromethane, tetrahydrofuran, 1,2-dimethoxyethane, butyl acetate, acetone, acetonitrile, 2-butanone, and dimethylsulfoxide.

In another embodiment, this disclosure provides a process for preparation of a compound of formula III:

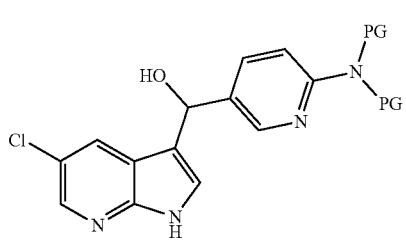

or a salt thereof;
comprising contacting a compound of formula A or a salt thereof, with a compound of formula B or a salt thereof:

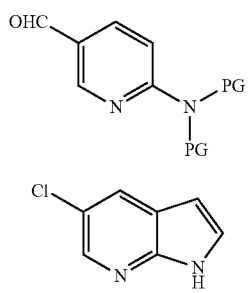

under addition conditions to provide the compound of formula III or a salt thereof, wherein each PG independently is a protecting group.

The addition conditions comprise a base and a catalyst. The non-limiting examples of the base include sodium carbonate, sodium bicarbonate, potassium carbonate, potassium bicarbonate, potassium-tert-butoxide, potassium tert-pentoxide, cesium carbonate, lithium-tert-butoxide, magnesium-tert-butoxide, sodium-tert-butoxide, potassium hydroxide and lithium hydroxide. The non-limiting examples of the catalyst include tetrabutylammonium hydrogen sulfate, tetrabutylammonium fluoride, tetrabutylammonium chloride, tetrabutylammonium bromide, tetrabutylammonium iodide, 18-crown-6 and 15-crown-5.

The addition conditions further comprise a solvent. The non-limiting examples of the solvent include isopropyl alcohol, toluene, acetonitrile, nitromethane, N,N-dimethylformamide, N,N-dimethylacetamide, dimethylsulfoxide, 3-methyl-1-butanol, 2-methoxyethanol, 2-propanol, and xylene.

The addition conditions further comprise a temperature of about 15-25° C.

A variety of protecting groups, PG, can be used in compound of formula A. The non-limiting examples of protecting groups for amines include t-butyloxycarbonyl (Boc), benzyloxycarbonyl (Cbz), 9-fluorenylmethoxycarbonyl (Fmoc), and the like. In one embodiment, PG is Boc.

In another embodiment, this disclosure provides a process for preparation of a compound of formula IV:

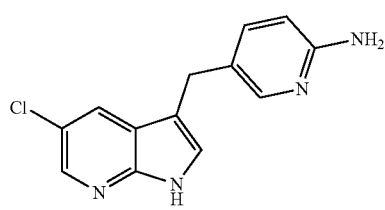

or a salt thereof;
comprising subjecting a compound of formula III:

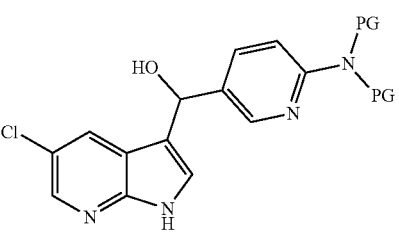

or a salt thereof, to N-deprotection and alcohol reduction conditions to provide the compound of formula IV or a salt thereof, wherein each PG independently is a protecting group.

A variety of protecting groups, PG, can be used in compound of formula III. The non-limiting examples of protecting groups for amines include t-butyloxycarbonyl (Boc), benzyloxycarbonyl (Cbz), 9-fluorenylmethoxycarbonyl (Fmoc), and the like. In one embodiment, PG is Boc.

The N-deprotection and alcohol reduction conditions of step b) comprise triethylsilane and trifluoroacetic acid.

The N-deprotection and alcohol reduction conditions further comprise a solvent. The non-limiting examples of the solvent include acetonitrile, 1,2-dichloroethane, dichloromethane, tetrahydrofuran, 1,2-dimethoxyethane, butyl acetate, acetone, 2-butanone, and dimethylsulfoxide.

In another embodiment, this disclosure provides a process for preparation of a compound of formula I:

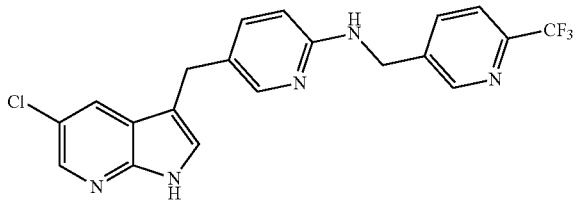

or a salt thereof;
comprising contacting a compound of formula IV:

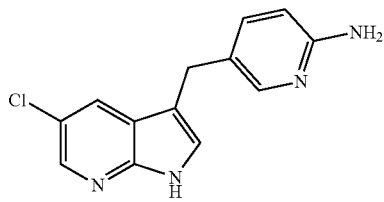

or a salt thereof;
with a compound of formula V:

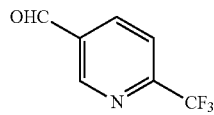

or a salt thereof,
under reductive amination conditions to provide the compound of formula I or a salt thereof.

The reductive amination conditions comprise triethylsilane and trifluoroacetic acid.

The reductive amination conditions further comprise a solvent. The non-limiting examples of the solvent include acetonitrile, 1,2-dichloroethane, dichloromethane, tetrahydrofuran, 1,2-dimethoxyethane, butyl acetate, acetone, acetonitrile, 2-butanone, and dimethylsulfoxide.

Compounds

In another embodiment, this disclosure provides a compound of formula III:

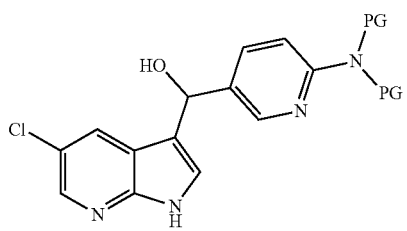

or a salt thereof, wherein each PG independently is a protecting group.

A variety of protecting groups, PG, can be used in compound of formula A. The non-limiting examples of protecting groups for amines include t-butyloxycarbonyl (Boc), benzyloxycarbonyl (Cbz), 9-fluorenylmethoxycarbonyl (Fmoc), and the like. In one embodiment, PG is Boc.

In another embodiment, this disclosure provides a compound of formula IV:

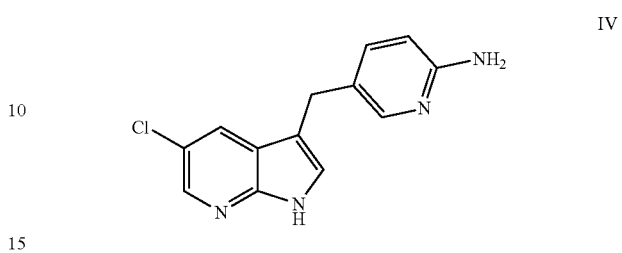

or a salt thereof.

In another embodiment, the salt of the compound of formula IV is a trifluoroacetic acid salt.

The intermediates in the process for the synthesis of formula I can be used in the next step with or without purification. The conventional means of purification include recrystallization, chromatography (e.g. adsorbant, ion exchange, and HPLC), and the like.

EXAMPLES

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of compounds described herein, may be accomplished as described in the following examples. If available, reagents may be purchased commercially, e.g. from Sigma Aldrich or other chemical suppliers. Unless otherwise noted, the starting materials for the following reactions may be obtained from commercial sources.

Examples related to the present invention are described below. In most cases, alternative techniques can be used. The examples are intended to be illustrative and are not limiting or restrictive to the scope of the invention.

Example 1. Synthesis of [5-(5-chloro-1H-pyrrolo[2,3-b]pyridin-3-ylmethyl)-pyridin-2-yl]-(6-trifluoromethyl-pyridin-3-ylmethyl)-amine

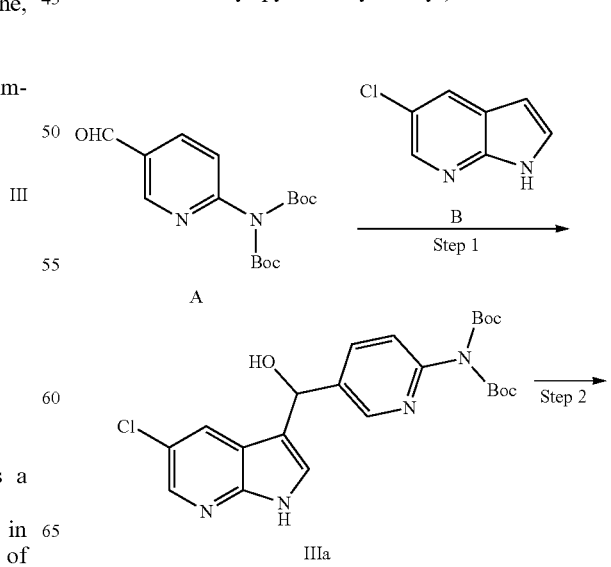

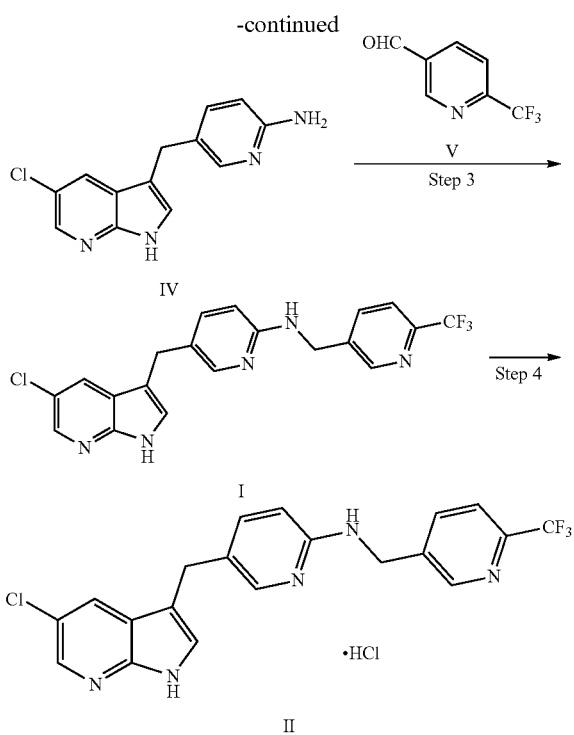

Step 1: Conversion of A to IIIa

The reactor was charged with Compound A (1000 gm, 1.0 eq.), Compound B (497 gm, 1.05 eq.), tetrabutylammonium hydrogen sulfate (31.6 gm, 0.03 eq.) and isopropanol (12 L, 11.8 vol). The reaction mixture was stirred for at least about an hour to obtain a near clear, yellow solution. Then potassium tert-pentoxide (73 mL, 0.04 eq.) was added over 30 seconds. The reaction mixture was stirred at about 15-25° C. for about 20-24 hours. The reaction was monitored by HPLC. When the content of compound IIIa was more than 80%, the reaction was deemed complete. The reaction mixture was cooled to about 0-10° C. and then stirred for at least about 2 hours. The precipitate was filtered, washed with 3 L isopropanol that had been cooled to 0° C. and dried to provide compound IIIa as a white solid (1.34 kg, 91.2% yield, 97.7% purity by HPLC). $^1$HNMR (DMSO-d6): δ (ppm) 11.8 (s, NH), 8.50-8.51 (d, 1H), 8.17 (d, 1H), 7.85-7.88 (dd, 1H), 7.82 (d, 1H), 7.41 (S, 1H), 7.29-7.31 (d, 1H), 6.04 (s, 2H), and 1.35 (s, 18H).

Alternatively, potassium tert-pentoxide can also be used in this reaction as a 25% solution in toluene.

Step 2: Conversion of IIIa to IV

The reactor was charged with compound IIIa (1.1 kg, 1 eq.) and acetonitrile (8.8 L, 12.4 vol) and the reaction mixture was stirred. Then triethylsilane (1.35 kg, 5 eq.) was added at about 15-30° C. over at least about 10 minutes. Then trifluoroacetic acid (2.38 kg, 9 eq.) was added to the reactor at about 15-30° C. over at least about 30 minutes. The reaction mixture was heated at about 55-65° C. over at least about 4 hours. It was then stirred at about 55-65° C. for about 20-48 hours. The reaction was monitored by HPLC. When the content of compound IIIa was less than about 1%, the reaction was deemed complete. The reaction mixture was cooled to about 45-55° C. and then a) concentrated to 3.3 L under vacuum and b) water (8.25 L) was charged. Steps a) and b) were repeated 4 times. The reaction mixture was then heated at about 45-60° C. and stirred for bout 1-3 hours. It was then cooled to about 0-10° C. over at least about 2 hours and it was stirred at about 0-10° C. for about 2-4 hours. The precipitate was filtered, washed with 2.2 L water and then with heptane (1.1 L) and dried to provide the TFA salt of compound IV as an off-white solid (673.3 gm, 77.9% yield, 99.7% purity by HPLC). $^1$H NMR (DMSO-d6): δ (ppm) 11.78 (s, COOH), 8.18 (d, 1H), 8.08-8.09 (broad doublet, 2H), 7.93-7.94 (d, 1H), 7.81-7.84 (dd, 1H), 7.47-7.48 (d, 1H), 6.90-6.93 (d, 1H), 3.92 (s, 2H).

Step 3: Conversion of IV to I

The reactor was charged with compound IV (663.3 gm, 1 eq.), compound V (623.2 gm, 2.0 eq.) and acetonitrile (13.3 L). The reaction mixture was stirred for about 5-10 minutes at room temperature. Triethylsilane (1531.6 gm, 7.4 eq.) was then added to the reactor over at least about 10 minutes at or less than about 30° C. Trifluoroacetic acid (1542.5 gm, 7.6 eq.) was added to the reactor over at least about 10 minutes at or less than about 30° C. The reaction mixture was stirred for at least about 30 minutes at about 15-30° C. It was then heated to about 70-82° C. over at least about one hour and then stirred at about 70-82° C. for about 20-48 hours. The reaction was monitored by HPLC. When the content of compound IV was less than about 1%, the reaction was deemed complete.

The reaction mixture was cooled to room temperature, the acetonitrile layer was separated and concentrated. Then water (7.96 L) was charged and the reaction mixture was concentrated to 6.64 L under vacuum providing a tri-phasic mixture. It was then cooled to 15-25° C., charged with ethyl acetate (10.6 L) and stirred providing a biphasic mixture. It was cooled to 0-10° C., charged with a 25% NaOH solution in water until a pH of about 8-9 was reached with vigorous stirring, heated to about 65-75° C. and stirred at about 65-75° for about 30 minutes. The organic layer was separated, and water (3.98 L) was charged and the reaction mixture was heated at about 65-75° C. The organic layer was separated and concentrated to about 5.3-5.9 L under vacuum, heptane (11.9 L) was added and the slurry was heated to about 55-65° C. and stirred for about 2 hours. The reaction mixture was cooled to about 15-30° C. over at least about 2 hours and then stirred at about 15-30° C. for at least about 1 hour. The precipitate was filtered, washed with heptane (1.99 L) and dried. The filter cake was charged into reactor with ethyl acetate (5.31 L, 8 vol) and heptane (2.65 L, 4 vol), cooled to about 15-30° C. over at least about 2 hours and then stirred at about 15-30° C. for at least about 1 hour. The precipitate was filtered, washed with heptane and dried to provide Compound I as a light yellow solid (648.4 gm, 89.4% yield, 99.4% purity by HPLC).

Step 4: Conversion of I to II

The reactor was charged with compound I (10 gm, 1 eq.), 110 mL ethanol was added and the reaction mixture was stirred. Concentrated hydrochloric acid (4.7 gm, 2 eq.) was slowly added to the reaction mixture while maintaining a temperature of about 30° C. or less to form a clear solution. It was then filtered and washed with methanol (10 mL). It was again filtered and purified water (3 mL) was added to it at about 28-32° C. The mixture was stirred at about 28-32° C. for 1-3 hours and filtered, purified water (177 mL) was added to it at about 25-32° C. The reaction mixture was cooled at about 0-7° C. and stirred for at least about 2 hours. Optionally, seed crystals of compound II can be added in this step. The solids were filtered, rinsed with a cool (0-5° C.) mixture of methanol (6 mL) and MTBE (24 mL), and with cool (0-5° C.) MTBE (30 mL). The product was dried to provide Compound II (90% yield).

The crystallization of Compound II to Form C was carried out using (A) 0.5.% volume/volume wet methyl tert-butyl ether (MTBE); (B) 1.0.% volume/volume wet MTBE; and (C) 1.5% volume/volume wet MTBE as described below. Form C, which was made by either crystallization procedure (A), (B) or (C) described below, was characterized by an X-ray powder diffractogram (XRPD) comprising peaks (±0.2°) at 7.1, 16.5, 20.8, 23.2 and 28.1° 2θ as determined on a diffractometer using Cu-Ka radiation. These peaks are consistent with the XRPD peaks of Form C that are described in U.S. Ser. No. 62/157,902 (±0.2°), filed on May 6, 2015, which is incorporated herein by reference in its entirety.

Procedure (A): Preparation of 0.5% Volume/Volume Wet MTBE (1000 mL):

(1) 5 mL of USP water was charged to 1000 mL volumetric flask and diluted with 1000 mL of MTBE. The resulting solution was stirred for about 30 minutes.

(2) A 500 mL 3 neck flask equipped with an overhead stirrer, nitrogen inlet, and condenser was charged with mechanically sieved Compound II. Compound II was mechanically sieved with a sieving machine.

(3) The reaction mixture was diluted with 0.5% v/v wet MTBE (300 mL, 15 vol) and stirred.

(4) The reaction mixture was slowly heated to reflux temperature (52-53° C.) and reflux was continued for about 24 hours. Agitation speed was increased as the reaction mixture thickened.

(5) Samples were pulled at 1 hour, 2 hours, 4 hours, 8 hours, 12 hours and 24 hours.

(6) The reaction mixture was cooled to room temperature and stirred for about 6 hours.

(7) The reaction mixture was filtered and the cake was washed the cake with MTBE (2 vol, 40 mL).

(8) The resulting product was dried at 40-45° C. overnight.

(9) The crystallized product was determined to be Form C by XRPD.

Procedure (B): Preparation of 1.0% Volume/Volume Wet MTBE (1000 mL):

(1) 10 mL of USP water was charged to 1000 mL volumetric flask and diluted with 1000 mL of MTBE. The resulting solution was stirred for about 60 minutes.

(2) A 500 mL 3 neck flask equipped with an overhead stirrer, nitrogen inlet, and condenser was charged with mechanically sieved Compound II. Compound II was mechanically sieved with a sieving maching.

(3) The reaction mixture was diluted with 1.0% v/v wet MTBE (300 mL, 15 vol) and stirred.

(4) The reaction mixture was slowly heated to reflux temperature (52-53° C.) and reflux was continued for about 24 hours. Agitation speed was increased as the reaction mixture thickened.

(5) Samples were pulled at 1 hour, 2 hours, 4 hours, 8 hours, 12 hours and 24 hours.

(6) The reaction mixture was cooled to room temperature and stirred for about 6 hours.

(7) The reaction mixture was filtered and the cake was washed the cake with MTBE (2 vol, 40 mL).

(8) The resulting product was dried at 40-45° C. overnight.

(9) The crystallized product was determined to be Form C by XRPD.

Procedure (C): Preparation of 1.0% Volume/Volume Wet MTBE (1000 mL):

(1) 15 mL of USP water was charged to 1000 mL volumetric flask and diluted with 1000 mL of MTBE. The resulting solution was stirred for about 60 minutes.

(2) A 500 mL 3 neck flask equipped with an overhead stirrer, nitrogen inlet, and condenser was charged with micronized compound II mechanically sieved Compound II. Compound II was mechanically sieved with a sieving maching.

(3) The reaction mixture was diluted with 1.0% v/v wet MTBE (300 mL, 15 vol) and stirred.

(4) The reaction mixture was slowly heated to reflux temperature (52-53° C.) and reflux was continued for about 24 hours. Agitation speed was increased as the reaction mixture thickened.

(5) Samples were pulled at 1 hour, 2 hours, 4 hours, 8 hours, 12 hours and 24 hours.

(6) The reaction mixture was cooled to room temperature and stirred for about 6 hours.

(7) The reaction mixture was filtered and the cake was washed the cake with MTBE (2 vol, 40 mL).

(8) The resulting product was dried at 40-45° C. overnight.

(9) The crystallized product was determined to be Form C by XRPD.

Another embodiment of this disclosure relates to process of preparing crystalline Form C of Compound II:

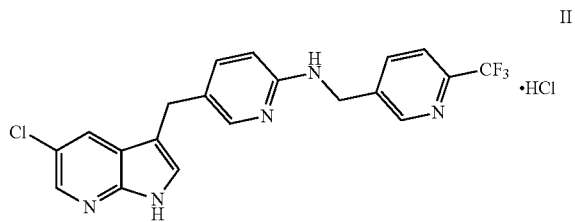 [SMILES: FC(F)(F)c1ccc(CNc2ccc(Cc3c[nH]c4ncc(Cl)cc34)cn2)cn1 ; Cl]

comprising:

(1) adding Compound II to from about 0.4% v/v wet MTBE to about 1.5% v/v wet MTBE to provide a reaction mixture;

(2) refluxing the reaction mixture;

(3) cooling the reaction mixture to about room temperature; and (4) isolating the crystalline Form C of Compound II from the reaction mixture.

For step (1), it will be understood that either Compound II can be added to wet MTEB, or wet MTEB can be added to Compound II.

In another embodiment of the of process of preparing crystalline Form C of Compound II, step (1) comprises adding Compound II to about 0.5% v/v wet MTBE to provide a reaction mixture.

In another embodiment of the of process of preparing crystalline Form C of Compound II, step (2) further comprises heating the reaction mixture to a temperature of about 52-53° C.

Another embodiment of this disclosure relates to a process of preparing crystalline Form C of Compound II, comprising the steps of:

(a) adding MTBE to USP water and optionally stirring, mixing or agitating the reaction mixture;

(b) diluting mechanically sieved Compound II with from about 0.4% v/v wet MTBE to about 1.5% v/v wet MTBE, and optionally stirring, mixing or agitating the reaction mixture;

(c) refluxing the reaction mixture, and optionally increasing the agitation, stirring or mixing;

(d) cooling the reaction mixture to about room temperature; and (e) isolating the cake from the reaction mixture and washing the cake with MTBE.

In another embodiment of the process of preparing crystalline Form C of Compound II, Compound II in step (a) is mechanically sieved with a sieving machine.

It will be understood that in step (a), Compound II can be added to wet MTBE, or wet MTBE can be added to Compound II.

In another embodiment of the process of preparing crystalline Form C of Compound II, step (b) comprises diluting mechanically sieved Compound II with about 0.5% v/v wet MTBE, and stirring, mixing or agitating the reaction mixture.

In another embodiment of the process of preparing crystalline Form C of Compound II, step (b) comprises diluting mechanically sieved Compound II with about 0.6% v/v wet MTBE, and stirring, mixing or agitating the reaction mixture.

In another embodiment of the process of preparing crystalline Form C of Compound II, step (b) comprises diluting mechanically sieved Compound II with about 0.7% v/v wet MTBE, and stirring, mixing or agitating the reaction mixture.

In another embodiment of the process of preparing crystalline Form C of Compound II, step (b) comprises diluting mechanically sieved Compound II with about 0.8% v/v wet MTBE, and stirring, mixing or agitating the reaction mixture.

In another embodiment of the process of preparing crystalline Form C of Compound II, step (b) comprises diluting mechanically sieved Compound II with about 0.9% v/v wet MTBE, and stirring, mixing or agitating the reaction mixture.

In another embodiment of the process of preparing crystalline Form of Compound II, step (b) comprises diluting mechanically sieved Compound II with about 1.0% v/v wet MTBE, and stirring, mixing or agitating the reaction mixture.

In another embodiment of the process of preparing crystalline Form C of Compound II, step (c) comprises heating the reaction mixture to a reflux temperature of about 50-56° C. and refluxing.

In another embodiment of the process of preparing crystalline Form C of Compound II, step (c) comprises heating the reaction mixture to a reflux temperature of about 52-53° C. and refluxing.

In another embodiment of the process of preparing crystalline Form C of Compound II, step (c) comprises heating reaction mixture to a reflux temperature of about 52-53° C., and refluxing for about 24 hours.

In another embodiment of the process of preparing crystalline Form C of Compound II, step (d) comprises cooling the reaction mixture to about room temperature and stirring the reaction mixture for about 4-8 hours.

In another embodiment of the process of preparing crystalline Form C of Compound II, step (d) comprises isolating the cake from the reaction mixture and washing the cake with MTBE.

In another embodiment of the process of preparing crystalline Form C of Compound II, the resulting product from step (e) is dried.

In another embodiment of the process of preparing crystalline Form C of Compound II, the resulting product from step (e) is dried at about 35-50° C. overnight.

In another embodiment of the process of preparing crystalline Form C of Compound II, the resulting product from step (e) is dried at about 40-45° C. overnight.

In another embodiment of the process of preparing crystalline Form C of Compound II, the crystalline Form C that is obtained from step (4) or step (e) is characterized by an X-ray powder diffractogram (XRPD) comprising peaks (±0.2°) at 7.1, 16.5, 20.8, 23.2 and 28.1 °2θ as determined on a diffractometer using Cu-Ka radiation.

All patents and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

The disclosure illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the disclosure using one of the terms, the disclosure also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described disclosure.

Thus, additional embodiments are within the scope of the disclosure and within the following claims.

What is claimed is:

1. A crystalline form of a compound of formula II:

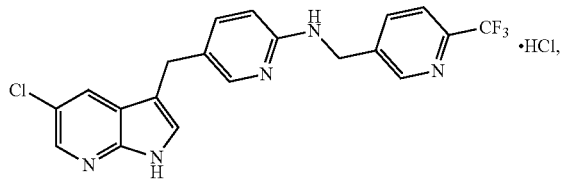

prepared by a process comprising:
(1) adding the compound of formula II to from about 0.4% v/v wet methyl tert-butyl ether to about 1.5% v/v wet methyl tert-butyl ether to provide a reaction mixture;
(2) refluxing the reaction mixture;
(3) cooling the reaction mixture to about room temperature; and
(4) isolating the crystalline form of the compound of formula II from the reaction mixture.

2. The crystalline form of the compound of formula II according to claim 1, wherein step (1) comprises adding the compound of formula II to about 0.5% v/v wet methyl tert-butyl ether to provide the reaction mixture.

3. The crystalline form of the compound of formula II according to claim 2, wherein step (2) further comprises heating the reaction mixture to a temperature of about 52-53° C.

4. The crystalline form of the compound of formula II according to claim 3, wherein the crystalline form of compound II is characterized by an X-ray powder diffractogram (XRPD) comprising peaks (±0.2°) at 7.1, 16.5, 20.8, 23.2 and 28.1 °2θ as determined on a diffractometer using Cu-Kα radiation.

5. The crystalline form of the compound of formula II according to claim 1, wherein the crystalline form of compound II is characterized by an X-ray powder diffractogram (XRPD) comprising peaks (±0.2°) at 7.1, 16.5, 20.8, 23.2 and 28.1 °2θ as determined on a diffractometer using Cu-Kα radiation.

* * * * *